United States Patent [19]
Kaufman

[11] Patent Number: 5,801,006
[45] Date of Patent: Sep. 1, 1998

US005801006A

[54] USE OF NADPH AND NADH ANALOGS IN THE MEASUREMENT OF ENZYME ACTIVITIES AND METABOLITES

[75] Inventor: Richard A. Kaufman, Bound Brook, N.J.

[73] Assignee: Specialty Assays, Inc., New Brunswick, N.J.

[21] Appl. No.: 795,283

[22] Filed: Feb. 4, 1997

[51] Int. Cl.$^6$ .............. C12Q 1/48; C12Q 1/00; C12Q 1/34; C12Q 1/42

[52] U.S. Cl. .............. 435/15; 435/4; 435/975; 435/18; 435/21; 435/12; 435/14; 435/26; 435/17; 536/27.6; 536/26.26; 536/26.7

[58] Field of Search .............. 435/15, 4, 975, 435/18, 21, 12, 14, 23, 26, 17; 536/27.6, 26.26, 26.7

[56] References Cited

U.S. PATENT DOCUMENTS

| | | | |
|---|---|---|---|
| 4,250,254 | 2/1981 | Modrovich | 435/15 |
| 4,271,264 | 6/1981 | Modrovich | 435/15 |
| 4,372,874 | 2/1983 | Modrovich | 435/15 |
| 4,394,449 | 7/1983 | Modrovich | 435/15 |
| 5,037,738 | 8/1991 | Lamos et al. | 435/15 |
| 5,116,728 | 5/1992 | Crowther et al. | 435/15 |
| 5,278,044 | 1/1994 | San George et al. | 435/15 |
| 5,589,348 | 12/1996 | Kaufman et al. | 435/26 |

OTHER PUBLICATIONS

Woenckhaus, C. et al "Preparation and Properties of NAD and NADP Analogs"; Pyridine Nucleotide Enzymes (Co–Enzymes and Co–Factors, vol. III) pp. 449–568 (1987) Dolphin et al, eds.

Stein, A. et al "The Thionicotinamide Analogs of DPN and TPN"; Biochemistry, vol. 2, No. 5, pp. 1015–1022 (Sep.–Oct. 1963).

Alivisatos, S. "Non–Enzymatic Interactions of Reduced Coenzyme I with Inorganic Phosphate and Certain Other Aninos"; Nature, No. 4948, pp. 973–975 (1964).

Kaplan, N., "the 3–Acetylpyridine Analog of DPN"; McCollum–Pratt Institute, No. 76, pp. 1713–1714 (1954).

Alivisatos, S., "Spontaneous Reactions of 1,3–Substituted 1,4–Dihydropyridines with Acids in Water at Neutrality ..."; Biochemistry, vol. 4, No. 12, pp. 2616–2630 (1965).

Wu, J., "Stability of NADPH: Effect of Various Factory on the Kinetics of Degradation"; Clinical Chemistry, vol. 32/2, pp. 314–319 (1968).

Zatman, L., "Effect of Isonicotinic Acid Hydrazides in Diphosphopyridine Nucleotidases"; J. Biol. Chem. No. 209, pp. 453–465 (1954).

Zatman, L., "The Isolation and Properties of the Isonitinic Acid Hydrazide Analogue of Diphosphopyridine Nucleotide"; J. Biol. Chem., No. 209, pp. 467–484 (1954).

Kaplan, N. et al "Reaction of Pyridine Nucleotide Analogues with Dehydrogenases"; J. Biol. Chem., No. 221, pp. 833–844 (1956).

Lowry, O. et al "The Stability of Pyridine Nucleotides"; J. Bio. Chem., vol. 236, No. 10, pp. 2756–2759 (1961).

Siegel, J. et al "Ultraviolet Absorption Sepctra of DPN and Analogs of DPN"; Archives of Biochemistry and Biophysics, No. 82, pp. 288–299 (1959).

Kaplan, N. et al "Chemistry and Properties of the 3–Acetylpyridine Analogue of Diphosphopyridine Nucleotide"; J. Biol. Chem., No. 221, pp. 823–832 (1956).

Primary Examiner—Louise N. Leary
Attorney, Agent, or Firm—Roberts & Mercanti, LLP

[57] ABSTRACT

Kits and methods for measuring enzyme activities and metabolites using NADH and NADPH analogs are disclosed. The analogs have extended stability in aqueous solutions and can used as replacements for NADH or NADPH cofactors in analytical procedures. Preferred aspects of the invention include kits containing the NADH and NADPH analogs for use in the measurement of ALT activity, AST activity, Urea, Ammonia, Salicylate, Triglycerides, Pyruvic Acid, Sorbitol Dehydrogenase activity, 5'-Nucleotidase activity, Creatine Kinase activity, 2,3-Diphosphoglyceric Acid, Adenosine 5'-triphosphate, α-Hydroxybutyrate Dehydrogenase activity, Lactate Dehydrogenase activity and the Carbon Dioxide content in analytical samples.

44 Claims, No Drawings

USE OF NADPH AND NADH ANALOGS IN THE MEASUREMENT OF ENZYME ACTIVITIES AND METABOLITES

TECHNICAL FIELD

The invention is directed to the use of NADPH (Nicotinamide Adenine Dinucleotide Phosphate) and NADH (Nicotinamide Adenine Dinucleotide) analogs as stable enzyme cofactors in the measurement of enzyme activities or in the measurement of substrates using enzymatic procedures which require the use of NADPH and/or NADH cofactors for their determination.

BACKGROUND OF THE INVENTION

The first reported preparation of NAD (nicotinamide adenine dinucleotide) analogs where a modification was made in the amide group of the pyridine ring of NAD was described in the literature by Zateman et al., J. Biol. Chem. 209, 453, 1954 and Zateman et al., J. Biol. Chem., 209, 467, 1954. The first NAD analog with a modification in the amide group of the pyridine ring that was functional with an enzyme was 3-acetylpyridine adenine dinucleotide which was synthesized by Kaplan et al., J. Biol. Chem. 221, 823, 1956. The NAD analogs were synthesized enzymatically using mammalian NAD glycohydrolase (NADase) which in addition to hydrolyzing the pyridine-glycoside bond of NAD can also perform an exchange reaction between the pyridine moiety of NAD and other substituted pyridines. Since these early studies at least 48 NAD/NADP analogs have been prepared where the amide group of the pyridine ring has been modified. For complete reviews of NAD/NADP analogs see The Pyridine Nucleotide Coenzymes by J. Everse, B. Anderson and W-S. You, Academic Press, New York, 1982, pp 92–132 and Pyridine Nucleotide Coenzymes (Coenzymes and Cofactors, Vol III), John Wiley, New York, 1987, pp 324–365, the contents of which are incorporated herein by reference. Of the NAD/NADP analogs with a modification of the amide group of the pyridine ring, only a few, however, are functional with dehydrogenase enzymes. The requirements for functionality with dehydrogenase enzymes is that a carbonyl or thiocarbonyl group must be present at the three position of the pyridine ring or that the amide group at the three position can be replaced by a halogen atom (see Everse et al. above).

Most of the enzymatic studies with the NAD/NADP analogs have been with the oxidized forms to elucidate the functional groups essential for binding and functionality with dehydrogenase enzymes (see reviews above). Kaplan et al., J. Biol. Chem., 221, 833, 1956 investigated the oxidation potentials of NAD analogs substituted at the three position with an aldehyde group (—CHO) and an acetyl group (–COCH$_3$) and found a potential for both groups of about –0.248 volts compared to –0.320 volts for NAD. Biellman et al. FEBS Lett. 7, 199, 1970 in similar studies found a potential of –0.285 volts for the thionicotinamide or thiocarbonyl NAD analog (–CSNH$_2$). Lamos et al. U. S. Pat. No. 5,037,738 used thionicotinamide-NADP and NADH in a simultaneous glucose and urea assay. In their procedure, glucose was measured in an enzymatic reaction using either glucose dehydrogenase or glucose-6-phosphate dehydrogenase by monitoring the increase in absorbance at 404 nm or increase in fluorescence at 550 nm due to the formation of thionicotinamide-NADPH while urea was determined in a coupled enzymatic procedure using urease and glutamate dehydrogenase by monitoring the decrease in absorbance at 340 nm or decrease in fluorescence at 440 nm which was due to the oxidation of NADH.

Abraham et al., Nature 203, 973, 1964; Biochemistry 4, 2616, 1965 investigated the spontaneous reactions of NADH with orthophosphates in neutral aqueous solutions by monitoring absorbance changes in the UV region of the spectrum where NADH absorbs. They observed that the reactivity of NADH increased with increasing concentrations of orthophosphates, and concluded from the changes in the UV absorbance that at least three consecutive reactions occurred from three successive protons transferred to NADH from orthophosphate. In one experiment, in 1.5 molar phosphate at pH 6.62 with NADH and 3-substituted pyridine-NADH analogs they observed the analogs were less reactive with phosphate than NADH.

In recent years, with the demand for increased specificity in clinical chemistry analyses, it has become common and well accepted that enzyme assays be measured in a kinetic or continuous mode while the reaction is occurring and for metabolite and substrate assays to be measured by an enzyme directly or indirectly using a coupled enzymatic procedure. Such procedures are well known to those acquainted with the art of clinical analyses. To illustrate two examples of kinetic or continuous monitoring of enzyme assays, consider the measurement of ALT (alanine aminotransferase) and AST (aspartate aminotransferase) enzyme activities.

ALT activity is typically measured using the following well established procedure:

L-alanine+α-ketoglutarate ALT→L-glutamate+pyruvic acid pyruvic acid+NADH Lactate Dehydrogenase→NAD+L-lactic acid In this procedure ALT activity is measured by the continuous monitoring of the pyruvic acid that is produced. This is accomplished by a coupled enzymatic reaction using lactate dehydrogenase to catalytically reduce the pyruvic acid to lactic acid with the concurrent oxidation of reduced nicotinamide adenine dinucleotide (NM)H) to its oxidized form, NAD. This reaction is measured spectrophotometrically by following the decrease in the absorbance (usually at 340 nm) which is due to the oxidation of NADH. NADH has an absorbance maxima in the UV region of the spectrum at about 340 nm while NAD has practically no absorbance at this wavelength.

AST activity is determined in a similar manner as follows:

L-aspartic acid+α-ketoglutarate AST→L-glutamate+oxaloacetate oxaloacetate+NADH Malate Dehydrogenase→NAD+L-malic acid In this procedure AST activity is measured by the continuous monitoring of the oxaloacetate that is produced. This is accomplished by a coupled enzymatic reaction using malate dehydrogenase to catalytically reduce the oxaloacetate to malic acid with the concurrent oxidation of NADH to its oxidized form, NAD. This reaction is measured spectrophotometrically by following the decrease in the absorbance (usually at 340 nm) which is due to the oxidation of NADH.

Examples of substrate and/or metabolite analyses that are measured using enzymatic procedures and which are coupled to the oxidation of NADH and/or NADPH are the determinations of carbon dioxide (collectively dissolved carbon dioxide, bicarbonate and carbonate), ammonia, pyruvic acid, urea or BUN (blood urea nitrogen), salicylates, triglycerides, adenosine 5'-triphosphate and 2,3-diphosphoglycerate. Carbon dioxide and urea are commonly measured using coupled enzyme reactions while ammonia is usually measured using the enzyme glutamate dehydrogenase and a reduced cofactor (usually NADPH) and pyruvic acid is usually measured using lactate dehydrogenase and NADH. Below are the procedures for measuring carbon dioxide, urea and ammonia.

Carbon Dioxide Procedure:

bicarbonate +

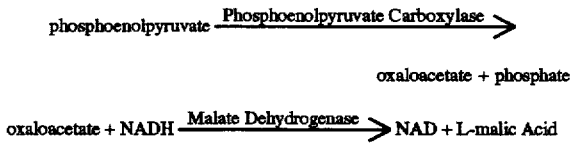

oxaloacetate + phosphate

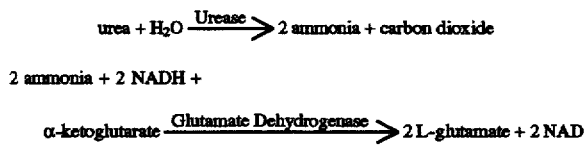

Carbon dioxide is usually measured as an endpoint reaction although a rate or kinetic assay is possible under certain conditions. There is a stochiometric relationship between the quantity of bicarbonate, or total carbon dioxide content, in the sample and the quantity of NADH oxidized. Thus by determining the decrease in absorbance, at usually 340 nm due to NADH oxidation by oxaloacetate, the quantity of bicarbonate in the sample can be determined.

Urea Procedure:

urea + $H_2O$ $\xrightarrow{Urease}$ 2 ammonia + carbon dioxide 2 ammonia + 2 NADH +

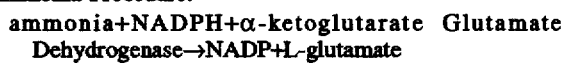

In this procedure there is a direct relationship between the quantity of urea in the sample and the quantity of NADH oxidized. In this coupled enzymatic procedure, 2 moles of NADH are oxidized for every 1 mole of urea in the sample. Although this reaction can be ran as an endpoint where all the urea has been converted to ammonia, and all the ammonia is converted to L-glutamate with the concurrent oxidation of a stochiometric quantity of NADH it is more commonly ran as a rate assay in clinical analyses. In this procedure, an absorbance reading is taken just after sample is added to the reagent and then a second absorbance reading at the same wavelength a short time later (typically 1 to 4 minutes) after the reaction has partially gone to completion. The latter absorbance reading is subtracted from the first absorbance reading to obtain the delta absorbance, $\Delta A$, for the time interval the reaction was allowed to proceed. This $\Delta A$ is compared with a standard of a known urea concentration and the urea concentration in the unknown can be determined. Alternatively, using the above procedure, several absorbance readings can be taken over the fixed time interval and from these, a linear regression can be performed to determine the average $\Delta A$ per time period or more typically the absorbance values are converted to the $\Delta A/min$. Also with this procedure, spectral interferences coming from the sample are eliminated, as long as the spectral interference doesn't change over the time interval being monitored, since they are eliminated when the absorbance readings are subtracted from one another.

Ammonia Procedure:

ammonia+NADPH+α-ketoglutarate Glutamate Dehydrogenase→NADP+L-glutamate

In clinical procedures for measuring ammonia, NADPH is usually used instead of NADH. This is done to prevent interference from pyruvic acid which may be present in the sample, which in the presence of lactate dehydrogenase which may also be present in the sample could catalyze the following reaction:

pyruvic acid+NADH Lactate Dehydrogenase→NAD+L-lactic acid

Since lactate dehydrogenase cannot use NADPH the interference from pyruvic acid is avoided.

In general, the above methods work very well. The major drawback with these methods is the inherent instability of NADH and NADPH in the aqueous reagent solutions. It is well known that NADH and NADPH only start to become relatively stable in aqueous solutions at a pH above 9 (Wu et al., Clin. Chem. 32, 314, 1986; Lowry et al., J. Biol. Chem. 235, 2756, 1961). Unfortunately, however, all the above methods are usually carried out at lower pH values. For example, the optimal pH for measuring ALT activity in serum is 7.5, for measuring AST activity in serum is pH 7.8, for measuring carbon dioxide in serum a pH 7.0 to about 8.0 is preferred, which is the optimum for the above coupled enzymatic reaction, and urea and ammonia assays in serum are typically measured at about pH 8.3, which is the optimum pH for the above two enzymatic procedures. For a more comprehensive discussion of reaction conditions for these and other analytes see Teitz, Textbook of Clinical Chemistry, 1986, W. B. Saunders Co. Philadelphia, Pa., the disclosure of which is incorporated herein by reference. Thus, aqueous solutions containing NADH and NADPH have only limited stability at the pH of these solutions and the reagents must be stored at refrigerator temperatures to maximize the shelf-life stability.

Some of the products that results from the instability of NADH and NADPH are the oxidation products, NAD and NADP, which can occur from oxidation by dissolved molecular oxygen in the aqueous solutions. In an effort to improve the stabilities of NADH and NADPH in aqueous solutions Modrovich (U. S. Pat. No. 4,394,449) added a nucleotide regenerating system to convert the oxidized enzyme cofactor back to the reduced form. Although this is helpful in extending the aqueous shelf-life of reagents containing NADH and NADPH cofactors, oxidation of the cofactors unfortunately is not the only degradative pathway. In other attempts to improve the shelf-life of NADH and NADPH, Modrovich (U. S. Pat. No. 4,372,894) added the reduced cofactors to a water miscible organic solvent along with a desiccant particle to keep the water content below 0.5%. In another method of stabilizing NADH, Crowther et al. (U. S. Pat. No. 5,116,728) used a buffering system to buffer the NADH concentration in an aqueous solution. In this system glucose, glucose dehydrogenase and NAD are added to an aqueous solution containing NADH. By choosing an appropriate pH glucose, NAD, and NADH concentrations, and glucose dehydrogenase activity, it is claimed that a relatively constant level of NADH can be maintained for some time. The contents of each of the foregoing U. S. Patents are hereby incorporated by reference.

Thus there is a need for better stability of diagnostic test kits in clinical chemistry laboratories that require the use of NADH and NADPH cofactors. Once the NADH and NADPH cofactors have degraded in the aqueous solutions in test kits, the reagent is no longer functional and has to be discarded if it is not used up before the expiration time with the clinical laboratory bearing the cost for the unused reagent and tests. Better cofactor stability will lengthen the shelf-life of aqueous reagents, reduce the cost per test (by being able to use all the reagent in a kit) and enhance to quality of the result due to having reagents of questionable stability.

SUMMARY OF THE INVENTION

In accordance with one aspect of the invention, the present invention includes a diagnostic reagent kit which includes a compound of the formula

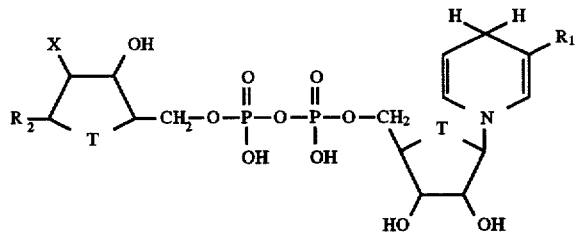

wherein:

R$_1$ is

R$_2$ is an aryl or heteroaryl;
Q is C or S;
T is O or S;
X is H, OR$_3$ or H$_2$PO$_4$, where R$_3$ is H, C$_{1-4}$ alkyl, C$_{1-4}$ haloalkyl, C$_{1-4}$ subtituted alkyl or halogen;
Y is O, S or NOH; and
Z is H, C$_{1-6}$ alkyl, C$_{1-6}$ haloalkyl, C$_{1-6}$ substituted alkyl, NHL where L is H, OH or NH$_2$, aryl or aralkyl.

In another preferred aspect of the invention, there is provided a method of quantifying the presence of an enzyme or analyte in a sample. The method includes:

a) contacting a sample with a compound of Formula I set forth above; and b) measuring the change of absorbance or fluorescence resulting from said contacting step a).

Some preferred NADPH and NADH cofactor analogs which have been found to be useful for measuring enzyme activities and substrates using enzymes requiring these cofactors, are 3-acetylpyridine adenine dinucleotide or 3-acetylpyridine-NADH; 3-acetylpyridine adenine dinucleotide phosphate or 3-acetylpyridine-NADPH; 3-pyridinealdehyde adenine dinucleotide or 3-pyridinealdehyde-NADH; 3-pyridinealdehyde adenine dinucleotide phosphate or 3-pyridinealdehyde-NADPH; thionicotinamide adenine dinucleotide or thionicotinamide-NADH; and thionicotinamide adenine dinucleotide phosphate or thionicotinamide-NADPH.

In preferred aspects of the invention, the NADH and NADPH analogs are included in kits and methods for determining the presence of metabolite or enzyme activity in an analytical sample. For example, ALT, AST, lactate dehydrogenase, α-hydroxybutyrate, creatine kinase, 5'-nucleotidase and sorbitol dehydrogenase activities can be determined in analytical samples using the analogs. In addition, the analogs can be used to determine carbon dioxide, ammonia, urea, pyruvic acid, salicylates, triglycerides, adenosine 5'-triphosphate and 2,3-diphosphoglycerate in an analytical sample.

Preferred cofactor analogs for determine urea in samples are 3-acetylpyridine-NADH 3-acetylpyridine-NADPH, 3-pyridinealdehyde-NADH and 3-pyridinealdehyde-NADPH.

One of the advantages of the present invention is that certain NADH and NADPH analogs such as 3-acetylpyridine-NADH, 3-pyridinealdehyde-NADH, and thionicotinamide-NADH are much more stable in aqueous solutions at acid, neutral, and alkaline pH's (i.e. from about <6 to about 10.5) than are NADH and NADPH. Thus, diagnostic reagent kits manufactured with these cofactor analogs have far superior shelf-lives than current conventional tests made with either NADH or NADPH.

Another advantage of the kits and methods of the invention is that the NADPH and NADH analogs are in the reduced form. Assays, for example like lactate dehydrogenase activity determinations, can be measured in the reverse direction (pyruvate→lactate) where the activity is about two fold higher than in the forward direction (lactate→pyruvate) with more stable kits and again less reagent waste since the forward reaction uses the oxidized cofactor which is relatively unstable at the optimal pH (~9) of the forward reaction.

Another significant advantage of the kits and methods of the invention is that the NADPH and NADH analogs give increased sensitivities in the assays. This is especially true for the determination of ammonia in serum and plasma where the upper end of the reference range is only about 60 micromoles per liter. By using, for example, thionicotinamide-NADH or thionicotinamide-NADPH instead of either NADH or NADPH, the sensitivity is increased by nearly a factor of two. Also the thionicotinamide analogs have absorbance maxima in the visible region of the spectrum and are less sensitive to turbidity in clinical samples caused by high levels of lipids (triglycerides) which interfere with absorbance measurements at 340 nm where NADH and NADPH are usually measured. Also, the increased sensitivity of the thionicotinamide NADH and NADPH analogs allows less sample volume to be used in assays. This is especially important when measuring clinical samples from infants and newborns where the sample volume is often limited.

DETAILED DESCRIPTION OF THE INVENTION

In one preferred aspect, the invention is directed to diagnostic kits containing NADH and NADPH analogs. The analogs are of the Formula: (I)

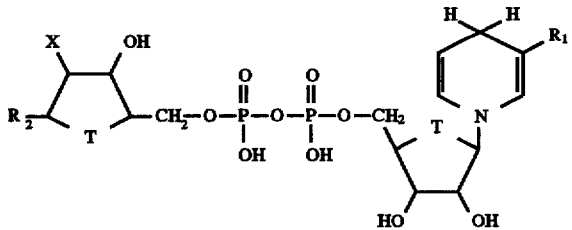

wherein:

Y

R$_1$ is

R$_2$ is an aryl or heteroaryl;
Q is C or S;
T is O or S;
X is H, OR$_3$ or H$_2$PO$_4$, where R$_3$ is H, C$_{1-4}$ alkyl, C$_{1-4}$ haloalkyl, C$_{1-4}$ subtituted alkyl or halogen;
Y is O, S or NOH; and Z is H, $C_{1-6}$ alkyl, $C_{1-6}$ haloalkyl, $C_{1-6}$ substituted alkyl, NHL where L is H, OH or $NH_2$, aryl or aralkyl.

Within Formula (I), $R_1$ is preferably selected from among the group:

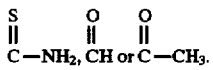

Alternatively, $R_1$ can be selected from among:

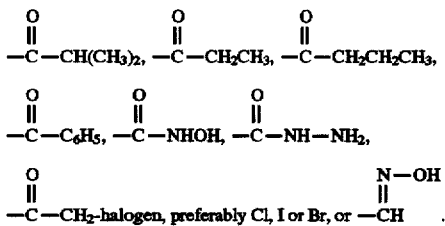

Preferably, $R_2$ is an adenine such as:

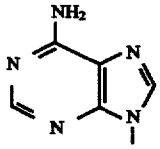

Alternatively, $R_2$ can be a substituted adenine, a substituted or unsubstituted member of the group consisting of xanthines, thioxanthines, hypoxanthines, guanines or other fused heterocyclic ring structures, aryls, substituted aryls, etc.

Also within Formula (I), X is preferably OH or $H_2PO_4$ and each T is O. Preferred compounds for inclusion with the kits and methods describe herein in accordance with Formula (I) include 3-pyridinealdehyde-NADH, 3-pyridinealdehyde-NADPH, 3-acetylpyridine-NADH, 3-acetylpyridine-NADPH thionicotinamide-NADH and thionicotinamide-NADPH. These compounds can be synthesized using standard organic chemistry techniques, or, if desired, purchased from commercial suppliers such as Sigma Chemical Co. It is contemplated that the kits of the present invention will include the compounds of Formula (I) in amounts ranging from about 0.01 to about 1.0 mmol/liter.

The kits and methods of the present invention are useful in the measurement of various enzyme activities and metabolites. A non-limiting list of such materials which can be measured using the synthetic analogs described herein include ALT (alanine aminotransferase) activity, AST (aspartate aminotransferase) activity, lactate dehydrogenase activity, α-hydroxybutyrate activity, sorbitol dehydrogenase activity, creatine kinase activity, 5'-nucleotidase activity, urea, ammonia, salicylates, triglycerides, pyruvic acid, carbon dioxide, 2,3-diphosphoglycerate and adenosine 5'-triphosphate content in analytical samples.

In additional aspects of the invention, the diagnostic kits also include an enzyme such as lactate dehydrogenase, malate dehydrogenase, phosphoenolpyruvate carboxylase, glutamate dehydrogenase, urease, salicylate hydroxylase, pyruvate kinase, phosphoglyceric phosphokinase, phosphoglycerate mutase, glycerol kinase, adenosine deaminase or glyceraldehyde phosphate dehydrogenase. The enzymes will be present in amounts sufficient to provide enzyme activities of from about 0.1 to about 150 Units/ml of the reagent containing solution. It will be understood that the actual amounts of enzyme activity will depend upon the enzyme(s) included in the kit and the target metabolite or enzyme activity sought to be measured.

Since the NADH/NADPH analogs of Formula (I) are not the "natural" cofactors commonly found in biological systems, the compatibility or functionality of the NADH/NADPH analogs with dehydrogenase enzymes are verified. For example, it was determined that in the case of 3-acetylpyridine-NADH, their are several suitable lactate dehydrogenases including those found in: chicken liver, rabbit muscle, porcine muscle, bovine muscle, chicken heart, porcine heart, Leuconostoc mesenteroides and Staphyloccus sp. It is contemplated other lactate dehydrogenases would be suitable as well. Similarly, the suitability or compatibility of the NADH/NADPH analogs with the malate dehydrogenase (MDH) was also verified and it was determined that for 3-acetylpyridine-NADH, for example, the malate dehydrogenases from Thermus sp. and porcine heart are suitable and that other species of enzyme are expected to be suitable.

In some kits, an oxamate can be included in place of an enzyme, such as lactate dehydrogenase for example, in amounts ranging from about 5 to about 25 mmol/liter.

The kits of the present invention can be prepared in either wet or dry form, including lyophilized form, depending upon the needs of the user. The kits can also include a suitable buffer such as tris(hydroxymethyl)aminomethane, tris(hydroxymethyl)aminomethane sulfate, bicine, Bis-Tris, Hepes, imidazole, and MES. It will be apparent to those of ordinary skill in the art that the buffer included will depend upon the preference of the artisan and will also be selected based on the metabolite or enzyme activity sought to be measured. It is contemplated, however that there will be sufficient buffer in the kits, i.e. from about 0.01 to about 1.0 mol/liter, and the analog-containing solution will have a pH of from about 5.5 to about 9.5.

In still further aspects of the invention, the diagnostic kits can contain a substrate such as L-alanine, α-ketoglutarate, L-aspartate, pyruvic acid, α-ketobutyrate, fructose, adenosine 5'-triphosphate, adenosine 5'-monophosphate, 2-phosphoglycolic acid, phosphoenolpyruvate, adenosine 5'-diphosphate and creatine. The substrates will be present in amounts of from about 0.1 mmol/liter to about 1000 mmol/liter. If desired, the kits can be prepared to include a suitable antimicrobial such as sodium azide, Kathon, Bronopol or parabens. Such antimicrobials can be present in amounts ranging from about 0.01 to about 0.5% by wt.

The kits of the present invention can also be prepared to include enzyme stabilization ingredients or reagent systems, i.e. enzymes and substrates, such as those set forth in U.S. Pat. No. 4,394,449 where an oxidized cofactor can be reduced back to its original reduced form by using an appropriate enzyme and substrate. The contents of this patent is incorporated by reference herein. Briefly stated, the enzymatic regeneration of oxidized cofactors back to their reduced form serves to make the already long-lasting reagent kits last even longer.

Examples of enzyme coupled reactions for a regeneration of the oxidized NAD(P) analogs is as follows:

1) with glucose-6-phosphate and glucose-6-phosphate dehydrogenase:

NAD(P)-Analog+glucose-6-phosphate Glucose-6-phosphate Dehydrogenase→NAD(P)H-analog+ phosphogluconic acid 2) with glucose and glucose dehydrogenase:

NAD(P)-analog+glucose Glucose-Dehydrogenase→NAD(P)H-analog+gluconic acid

In the above examples the (P) denotes either the NAD analog or the phosphorylated analog, NADP. The above NAD(P)-analog regenerating systems is not meant to be exclusive of other enzyme-substrate systems, but only serves as examples.

The pyridine nucleotide regenerating system has also been found to extend the stability of reduced pyridine nucleotide cofactor analogs in other reagents. Reagents using NADH/NADPH analogs where improvements in analog stability was observed were with: ammonia, urea or BUN, ALT and AST and carbon dioxide.

Reagents in accordance with the present invention can be configured in several different formats. A single vial may be prepared which contains all necessary components including an antimicrobial, buffer and components to stabilize the coupling enzyme(s), if present. For convenience, a single vial ready-to-use liquid reagent is preferred with a storage temperature of about+2° to+8° C. (refrigerator storage). Alternatively, the reagents may be prepared as a two component system or even a three or more component system and as powder (dry-fill) or lyophilizate. Having components of the reagent in separate vials or bottles usually results in better component stability, but may be deemed less convenient by some end users.

EXAMPLES

The following non-limiting examples illustrate certain aspects of the invention. All parts and percentages are by weight unless otherwise noted and all temperatures are in degrees Celsius. The principal reagents were obtained from commercial suppliers such as Sigma Chemical Co.

The reagent compositions given below are the final concentrations of all ingredients after taking into account the sample volume. It is understood that the reagents can be made with varying degrees of concentration. For example, a concentrated version of the reagent can be prepared and then diluted with distilled, deionized, purified or nonpurified water before the reagent is used.

1. Determination of ALT Activity.

The following is an example of a reagent composition for the determination of ALT activity in an analytical sample using 3-acetylpyridine-NADH. There are many variations of this basic reagent but they all accomplish the same purpose which is the determination of the ALT activity in an analytical sample. The formulation chosen here is the IFCC recommended formulation (International Federation of Clinical Chemistry) with the exception that pyridoxal phosphate has been omitted and the cofactor NADH has been replaced with 3-acetylpyridine-NADH. The pyridoxal phosphate in the IFCC reagent formulation is to ensure that all the ALT holoenzyme in the sample has bound pyridoxal phosphate to insure that all the ALT activity in the sample is measured.

The coupled enzyme reaction for measuring ALT activity is as follows:

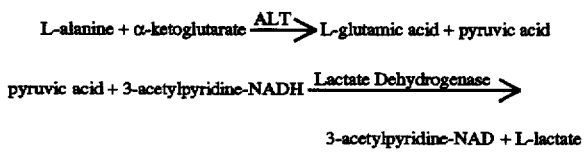

Reagent Composition (concentrations of components including sample volume)

| Ingredient | Concentration | Acceptable |
|---|---|---|
| tris(hydroxymethyl)amino-methane | 100 mmol/L | 10–500 mmol/L |
| L-alanine | 500 mmol/L | 200–800 mmol/L |
| α-ketoglutarate | 15 mmol/L | 5–50 mmol/L |
| lactate dehydrogenase | 26,000 U/L | >600 U/L |
| sodium azide | 0.06% w/v | 0.03–0.5% w/v |
| 3-acetylpyridine-NADH | 0.5 mmol/L | 0.1–1.0 mmol/L |
| pH | 7.5 | 7–8 |
| Ratio: sample volume/total volume | 1/12 | 1/5–1/100 |

Although the above example is with 3-acetylpyridine-NADH, thionicotinamide-NADH could be used in similar amounts as well as other analogs of Formula(I), if desired. The phosphorylated cofactor of NADH, NADPH, typically is not functional with lactate dehydrogenase. Thus, for the phosphorylated analogs, 3-acetylpyridine-NADPH, 3-pyridinealdehyde-NADPH and thionicotinamide-NADPH to be functional in the above reaction scheme, a suitable lactate dehydrogenase that uses phosphorylated cofactors would be necessary.

To determine ALT activity using the cofactor analogs the decrease in absorbance is followed spectrophotometrically as is normally done when using the NADH cofactor. The cofactor analogs have somewhat different wavelength maxima and molar absorbtivities, however, than NADH. Therefore, the factors which are used to convert the absorbance change per minute (ΔA/min) will be different for each cofactor analog and of course different from NADH. The wavelength absorbance maximum in the near-UV for 3-acetylpyridine-NADH is about 363 nm and for 3-pyridinealdehyde-NADH about 358 nm (Siegel et al., Arch Biochem and Biophys. 82, 288, 1959). For thionicotinamide-NADH which absorbs in the visible region of the spectrum, the wavelength maximum is about 398 nm (Stein et al. Biochem. 2, 5, 1015, 1063). At these wavelengths, the molar absorbtivities are about $9.1 \times 10_3$, $9.3 \times 10^3$ and $11.9 \times 10_3$ respectively for the three cofactor analogs. For comparison, the molar absorbtivity of NADH is $6.2 \times 10_3$ at 340 nm. Since most clinical chemistry analyzers have been designed to measure NADH/NADPH, the 340 nm wavelength is the closest wavelength to the absorbance maxima for 3-acetylpyridine-NADH and 3-pyridinealdehyde-NADH, although some analyzers have wavelengths between 340 and 405 nm, e.g. 360 and 380 nm. At 340 nm the absorbance of 3-acetylpyridine-NADH is about 92% of the absorbance of NADH and about 70% of the absorbance maxima at 363 nm. At 340 nm the absorbance of 3-pyridinealdehyde-NADH is about 94% of the absorbance of NADH and about 82% of the absorbance maxima at 358 nm. Thus, by measuring the decrease in absorbance at 340 nm, the factor to determine ALT activity needs to adjusted for the cofactor analog being used. For the thionicotinamide cofactor, however, most clinical chemistry analyzers have a wavelength at about 405 nm which is very near the wavelength maxima of 398 nm for this cofactor analog. Thus thionicotinamide-NADH can conveniently be measured by virtually all clinical chemistry analyzers at 405 nm.

When using the NADH cofactor analogs in the ALT coupled reaction above, sufficient activity of the coupling enzyme, in this case lactate dehydrogenase, must be added so that the secondary reaction (in this case the reduction of pyruvate to lactate and the concurrent oxidation of the reduced cofactor) is following the rate of the primary transamination reaction, especially samples with high ALT activities. In the reagent composition above, sufficient lactate dehydrogenase was added to give an assay linearity of 700 U/L. Addition of less enzyme activity will result in ALT lower linearity.

2. Determination of AST Activity.

The following is an example of a reagent composition for the determination of AST activity in an analytical sample using 3-acetylpyridine-NADH. As with the ALT reagent, there are many variations of this basic reagent. The formulation chosen here is the IFCC recommended formulation with the exception that pyridoxal phosphate and lactate dehydrogenase have been omitted and the NADH has been replaced by 3-acetylpyridine-NADH. As with the ALT reagent, the pyridoxal phosphate has been added to ensure that all the AST holoenzyme is saturated with pyridoxal phosphate so that all the active AST activity is measured. Lactate dehydrogenase is added to metabolize small amounts of pyruvic acid, during the lag phase of the reaction, which may be present in the sample, especially serum samples. As an alternative, sodium oxamate can be added to the reagent which inhibits lactate dehydrogenase that may be present in the sample and thus this is an alternative method of preventing interference by pyruvic acid.

The coupled enzyme reaction for measuring AST activity is as follows:

L-aspartic acid + α-ketoglutarate $\xrightarrow{AST}$ L-glutamic acid + oxaloacetate

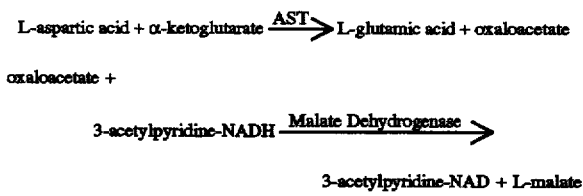

Reagent Composition (concentration of components including sample volume)

| Ingredient | Concentration | Acceptable |
|---|---|---|
| tris(hydroxymethyl)amino-methane | 80 mmol/L | 10–500 mmol/L |
| L-aspartate | 240 mmol/L | 100–500 mmol/L |
| α-ketoglutarate | 12 mmol/L | 5–50 mmol/L |
| malate dehydrogenase | 26,000 U/L | >600 U/L |
| sodium oxamate | 10 mmol/L | 5–25 mmol/L |
| sodium azide | 0.06% w/v | 0.03–0.5% w/v |
| 3-acetylpyridine-NADH | 0.5 mmol/L | 0.1–1.0 mmol/L |
| pH | 7.8 | 7.3–8.2 |
| Ratio: sample volume/total volume | 1/12 | 1/5–1/100 |

Much of the same discussion above in Example 1 for ALT is also applicable to the determination of AST activity. As an alternative to 3-acetylpyridine-NADH, thionicotinamide-NADH as well as other analogs of Formula (I) could also be used, if desired.

The phosphorylated derivatives of the cofactor analogs could be used as long as a suitable malate dehydrogenase can be found which will use the above phosphorylated cofactor analogs.

To determine AST activity using the cofactor analogs, the decrease in absorbance is followed spectrophotometrically as is normally done when using the NADH cofactor. Since the cofactor analogs have their maximum absorbance at different wavelengths than NADH as well as different molar absorbtivities, the factor used to convert the absorbance change per minute (ΔA/min) to Units per Liter (U/L) will be different for each cofactor and different from NADH (See the discussion for ALT activity determination for details on the molar absorbtivities of the cofactor analogs at their maxima in the near-UV and their sensitivities compared with NADH at 340 nm.)

When using the cofactor analogs in the AST coupled reaction, sufficient activity of the coupling enzyme, is this case malate dehydrogenase, must be added so that the secondary reaction (in this case the reduction of oxaloacetate to malate) is following the rate of the primary transamination reaction, especially samples with high AST activities. In the reagent composition above, sufficient malate dehydrogenase was added to give an assay linearity of 700 U/L. Addition of less enzyme activity gives lower AST linearity.

3. Determination of Ammonia Concentration.

The following is an example of a reagent composition that can be used for the determination of the ammonia concentration in an analytical sample. As with the ALT and AST reagents above there are many variations, but the distinctive feature in this formulation is the use of NADH and NADPH analogs.

The methodology used to measure ammonia in an analytical is based on the following reaction:

ammonia+α-ketoglutarate+3-acetylpyridine-NAD(P)H 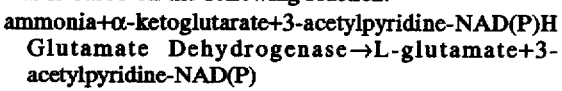 L-glutamate+3-acetylpyridine-NAD(P)

Reagent Composition (concentrations of components accounting for sample volume)

| Ingredient | Concentration | Acceptable |
|---|---|---|
| bicine(N,N-bis[hydroxyethyl]-glycine) | 0.2 mol/L | 0.01–0.6 mol/L |
| EDTA (ethylenediaminetetraacetic acid) | 0.07 mmol/L | 0–10 mmol/L |
| adenosine 5'-diphosphate | 3.3 mmol/L | 0–10 mmol/L |
| xylitol | 20% w/v | 0–30% w/v |
| bovine serum albumin | 0.07% w/v | 0.01–1% w/v |
| sodium azide | 0.07% w/v | 0.03–0.5% w/v |
| glutamate dehydrogenase | 50,000 U/L | >1,000 U/L |
| α-ketoglutarate | 27 mmol/L | 5–75 mmol/L |
| 3-acetylpyridine-NADH | 0.4 mmol/L | 0.1 to 1 mmol/L |
| pH | 8.3 | 6–9.3 |

In the above reaction scheme 3-acetylpyridine-NADH or the phosphorylated analog 3-acetylpyridine-NADPH was illustrated. Thionicotinamide-NADH, thionicotinamide-NADPH, 3-pyridinealdehyde-NADH and 3-pyridinealdehyde-NADPH, for example, can also be used. Of the three NADH/NADPH analogs, the thionicotinamides and 3-acetylpyridines exhibit a more favorable equilibrium for reduction of α-ketoglutarate. The thionicotinamide analogs are preferred for the determination of ammonia in clinical samples due to their increased sensitivity and the relatively low ammonia concentrations in clinical samples.

Ammonia concentrations is analytical samples may be determined in a number of ways using the above reaction scheme. Typically, the ammonia content in a sample is measured as an end point reaction. Since all the above mentioned NADH/NADPH cofactor analogs have absorbance maxima in the visible (reduced thionicotinamide) and near-UV (reduced 3-acetyl- and 3-pyridinealdehyde analogs) regions of the spectrum, the decrease in the absorbance of the reagent after sample has been added will be proportional to the ammonia level in the sample, after correcting for the effect of any absorbing compounds in the sample itself. Usually the reaction is allowed to go to completion or very near completion. (See the discussion under ALT for the choice of wavelengths and their molar absorbtivities and sensitivities).

Alternatively, the ammonia concentration may be determined as an initial rate assay. In these procedures the change in absorbance at an appropriate wavelength is determined as a function of time just after the sample containing the ammonia has been added to the reagent. Usually the reaction is followed for a short period of time, perhaps after only 20 to 50% of the ammonia has been consumed. The rate of ammonia metabolized and hence the rate of cofactor consumption will be proportional to the ammonia level. In order for initial rate assays to work, however, the conditions of the reaction have to be such that the reaction is basically a first order reaction with respect to the ammonia concentration. The above formulation is designed to work as an end point reaction.

When using the reduced 3-pyridinealdehyde analogs, it is preferable to measure the ammonia using an initial rate assay since the reaction tends to reach a point of equilibrium rather than go to completion.

Also in the above reaction scheme, it may be preferable to use the reduced phosphorylated pyridine analogs, especially if biological samples are being analyzed which may contain pyruvic acid and lactate dehydrogenase. A possible side reaction between pyruvic acid and the reduced cofactor analogs, catalyzed by lactate dehydrogenase, may occur which would cause a positive interference resulting in over-recovery of the ammonia content in the sample.

Alternatively, the NADH cofactor analogs could also be used in an assay for ammonia with pyruvic acid and lactate dehydrogenase present, but a lactate dehydrogenase inhibitor, such as oxamate could be added to inhibit the above reaction and prevent the oxidation of the NADH cofactor analogs by pyruvic acid. In the example above, 3-pyridinealdehyde-NAD(P)H and thionicotinamide-NAD(P)H could also be used in place of 3-acetylpyridine-NAD(P)H with thionicotnamide-NADPH preferred for measuring ammonia in clinical samples, furthermore, thionicotinamide-NADPH in conjunction with an enzyme regeneration system such as that disclosed herein is more preferred.

4. Determination of Urea Concentration

The following is an example of a reagent composition that can be used for the determination of the urea concentration in an analytical sample. Again, there are many variations of this basic reaction scheme, but the distinctive feature of this formulation is the use of the NADH/NADPH cofactor analogs. The methodology used to measure urea concentration in an analytical sample is based on the following reaction:

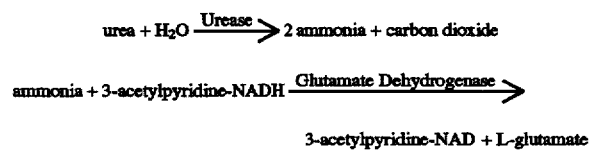

Reagent Composition (concentrations of components including sample volume)

| Ingredients | Concentration | Acceptable |
|---|---|---|
| bicine(N,N-bis[2-hydroxyethyl]-glycine) | 51 mmol/L | 10–500 mmol/L |
| EDTA (ethylenediaminetetraacetic acid) | 0.051 mmol/L | 0–10 mmol/L |
| adenosine 5'-diphosphate | 2.56 mmol/L | 0–10 mmol/L |

-continued

| Ingredients | Concentration | Acceptable |
|---|---|---|
| bovine serum albumin | 0.051% w/v | 0.01–1% w/v |
| xylitol | 15% w/v | 0–30% w/v |
| α-ketoglutarate | 20.5 mmol/L | 5–75 mmol/L |
| sodium azide | 0.026% w/v | 0.03–0.5% w/v |
| 3-acetylpyridine-NADH | 0.4 mmol/L | 0.1–1 mmol/L |
| urease | 25,800 U/L | 2,500–50,000 U/L |
| glutamate dehydrogenase | 7,700 U/L | 2,000–16,000 U/L |
| pH | 8.3 | 6.5–9.3 |

In the above reaction scheme 3-acetylpyridine-NADH is illustrated. Phosphorylated analogs, such as 3-acetylpyridine-NADPH, or 3-pyridinealdehyde-NAD(P)H and thionicotinamide-NAD(P)H can also be used. The same discussion as in the ALT reaction with regard to choice of wavelengths, absorbance maxima, and sensitivities and cofactor molar absorbtivities applies to this reaction as well.

For the methodology illustrated above, the urea concentration or BUN (blood urea nitrogen as it is sometimes referred) is determined spectrophotometrically by following the oxidation (usually the rate of oxidation) of the cofactor. Although it is possible to allow the reaction to proceed to completion, it is more customary to perform urea assays as a rate, especially in biological samples such as serum, so a larger dynamic reaction range can be obtained. To perform a urea determination as a rate procedure, the sample is mixed with reagent and absorbance measurements at an appropriate wavelength are taken as a function of time for a given time interval. From the absorbance change per unit of time, usually expressed as the ΔA per minute, the concentration of urea in an analytical sample can be obtained. Usually a standard is ran under the same conditions as the unknown and from the ΔA per minute of the standard the concentration of urea in the unknown can be calculated. As with the ammonia determination, for a rate assay conditions of the assay have to be optimized so that the ΔA per minute is proportional to the urea concentration.

For a urea end point assay, an absorbance reading at an appropriate wavelength is taken either before sample is added, or immediately after sample is added before a significant portion of cofactor is oxidized. After a period of time when the reaction has reached end point a second absorbance reading at the same wavelength is taken and the two absorbance readings are subtracted from each other to obtain the ΔA for the sample. If the sample background has an appreciable absorbance at the wavelength chosen for absorbance readings, a separate sample blank may be necessary for the case where the sample was added after the initial absorbance reading was taken. Typically a standard of known urea concentration is used for calibrating the assay. The ΔA of the unknown samples are then converted to urea concentrations knowing the ΔA and urea concentration of the standard.

5. Determination of the Carbon Dioxide Content

The following is an example of a reagent composition that can be used for the determination of the carbon dioxide content in an analytical sample. The carbon dioxide content or "total $CO_2$" as it is sometimes called is a measure of the bicarbonate, dissolved carbon dioxide and carbonate in an analytical sample. There are many variations of the methodology given below, but the distinctive feature given here is the use of the NADH analogs.

The methodology used to measure the carbon dioxide content in an analytical sample is based on the following reaction:

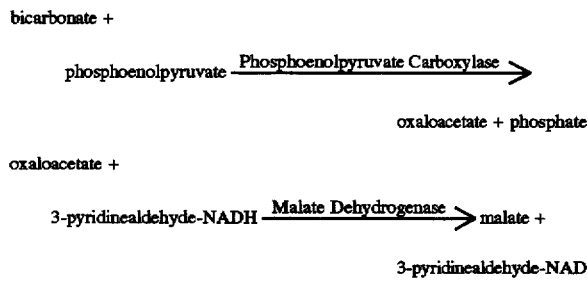

Reagent Composition (concentrations of components including sample volume)

| Ingredient | Concentration | Acceptable |
|---|---|---|
| tris(hydroxymethyl)amino-methane sulfate | 51 mmol/L | 10–500 mmol/L |
| magnesium chloride | 10 mmol/L | 2–20 mmol/L |
| EDTA (ethylenediaminetetraacetic acid) | 0.05 mmol/L | 0–10 mmol/L |
| bovine gamma globulin | 0.05% w/v | 0.01–1% w/v |
| sorbitol | 15% w/v | 0–30% w/v |
| phosphoenolpyruvate | 4 mmol/L | 1–10 mmol/L |
| phosphoenolpyruvate carboxylase | 3560 U/L | 500–10,000 U/L |
| malate dehydrogenase | 30,000 U/L | >1,000 U/L |
| sodium azide | 0.05% w/v | 0.03–0.5% w/v |
| 3-pyridinealdehyde-NADH | 0.5 mmol/L | 0.1–1 mmol/L |
| pH | 7.0 | 5.5–9.0 |

In the above formulation, 3-pyridinealdehyde-NADH was used as the cofactor for malate dehydrogenase, however 3-acetylpyridine-NADH and thionicotinamide-NADH can also be used. The reduced phosphorylated cofactors could also be used if a malate dehydrogenase is found that is functional with the phosphorylated analogs. Other divalent metals such as manganese can be used in place of the magnesium dichloride, if desired.

A "total carbon dioxide" determination in an analytical sample may be performed as an endpoint or as a rate assay using the above reaction scheme. For rate assays, the reaction components must be configured in such a way that the reaction is first order with respect to the "total carbon dioxide" content. For a rate assay, the absorbance at an appropriate wavelength is monitored over a given time interval immediately after the sample has been added and the ΔA usually expressed as per minute is calculated. By assaying a carbon dioxide standard under the same reaction conditions, it is relatively straight forward to calculate the carbon dioxide concentration of the unknown sample knowing the concentration and ΔA of the standard. An endpoint assay is performed in the same manner as for ammonia discussed above.

EXAMPLE 6

2 Component Liquid Total Carbon Dioxide Reagent

A two component liquid carbon dioxide reagent was prepared as follows:

Component 1: To ~50 mL deionized water is added 3.4 g Tris sulfate which is stirred until dissolved. Thirty grams of sorbitol is added along with deionized water until the volume is about 90 ml. Add 233 mg magnesium chloride and 3.7 mg Na$_2$EDTA.2H$_2$O and stir until dissolved. Adjust the pH to 7.0 with 50% NaOH and add 100 mg bovine gamma globulin, 90 mg sodium azide, stir until completely dissolved and dilute to 100 ml with deionized water. To 66 mls of this solution is added the following: 4026 Units malate dehydrogenase (Thermus sp.), 488 Units phosphoenolpyruvate carboxylase (from microorganism—Toyobo Co. Ltd.) and 50 Units glucose-6-phosphate dehydrogenase. The solution was divided as follows: to two 12.0 ml portions was added 150 ul of an aqueous 100 mmol/L glucose-6-phosphate solution and to a 30.0 ml portion was added 375 ul of the glucose-6-phosphate solution. To one of the 12.0 ml solutions is added 11.0 mg 3-acetylpyridine-NAD, to the other 12.0 ml aliquot is added 11.3 mg thionicotinamide-NAD, and to the 30.0 ml aliquot was added 25.1 mg 3-pyridinealdehyde-NAD. To a third 12.0 ml aliquot was added 10.9 mg NADH for comparative purposes. The 3-acetylpyridine-NAD and 3-pyridinealdehyde-NAD solutions were tightly capped and placed at 37° C. until the absorbance was constant at 340 nm—approximately 12 hours for the acetyl analog and 24 hours for the aldehyde analog.

Component 2: To ~5 mls deionized water was added 94.6 mg of the monocyclohexyl-ammonium salt of phosphoenolpyruvate. The pH was adjusted to 7.0 with 50% sodium hydroxide.

The four Component 1 solutions were transferred to 4 ml polyethylene bottles and placed at 37° C. after determining the amount of cofactor present. This was accomplished by mixing 100 ul of Component 1 with 33 ul Component 2 and adding 110 ul deionized water and 2 ul of a 1 mol/L sodium carbonate sample. The quantity of cofactor, expressed as the absorbance change (ΔA) due to the complete oxidation of the cofactor, was calculated by subtracting the absorbance of the solution 12 minutes after sample addition from the absorbance of a reference cuvette 4.5 seconds after a deionized water sample was added. Results of the 37° C. incubation are as follows:

| | ΔA at 340 nm except thionicotinamide-NADH ΔA at 405 nm | | | | | | |
|---|---|---|---|---|---|---|---|
| Days at 37° C. | 0 | 7 | 15 | 23 | 29 | 30 | 36 |
| 3-pyridinealdehyde-NADH | 1.66 | 1.59 | 1.62 | 1.41 | 1.34 | — | 1.34 |
| 3-acetylpyridine-NADH | 1.16 | 0.93 | 0.77 | 0.55 | | 0.30 | |
| thionicotinamide-NADH | 2.03 | 0.96 | 0.45 | — | — | — | |
| NADH | 1.22 | 0.09 | — | — | — | — | |

As can be seen from the data, about 7% of the NADH is left after 7 days at 37° C. In comparison, 96% of the 3-pyridinealdehyde-NADH, 80% of the 3-acetylpyridine-NADH and 47% of the thionicotinamide-NADH is still left during the same time period. Even after 36 days, 81% of 3-pyridinealdehyde-NADH is still left in the solution.

Below are the performances of the NADH cofactor analogs in the determination of the carbon dioxide content in a series of aqueous sodium carbonate samples.

| | ΔA 340 nm except for thionicotinamide-NADH 405 nm (measuring interval = 4.5 sec after sample addition to 975 sec) | | |
|---|---|---|---|
| Na$_2$CO$_3$ mmol/L | 3-pyridinealdehyde-NADH | 3-acetylpyridine-NADH | thionicotinamide-NADH |
| 10 | 0.281 | 0.371 | 0.306 |
| 20 | 0.672 | 0.631 | 0.595 |
| 30 | 1.066 | 0.896 | 0.949 |
| 40 | 1.436 | 1.158 | 1.268 |

The data demonstrates a linear relationship between the change in absorbance, ΔA, and the sodium carbonate concentration.

EXAMPLE 7

One Component Liquid Total Carbon Dioxide Reagent

To ~50 ml deionized water is added 3.4 g Tris sulfate. Thirty grams of sorbitol is added followed by deionized water to bring the volume to ~90 ml. Magnesium chloride, 190.4 mg and 3.7 mg $Na_2EDTA.2H_2O$ are added and stirred to dissolve. The pH is adjusted to 6.9 and 100 mg bovine gamma globulin and 90 mg sodium azide are added and after dissolving and adjusting the pH to 7.0, diluted to 100 ml with deionized water. To 10 mls of the solution was added 10.7 mg 3-pyridinealdehyde-NAD, 4.6 mg glucose-6-phosphate (sodium salt), 5 Units glucose-6-phosphate dehydrogenase and the solution was incubated at 37° C. for 24 hours. Sodium phosphoenolpyruvate hydrate, 16.6 mg, was added followed by 610 Units malate dehydrogenase and 74 Units phosphoenolpyruvate carboxylase.

The reagent was used to determine the total carbon dioxide concentration in a set of aqueous sodium carbonate samples by adding 2.0 ul sample to 140 ul of reagent and 93 ul deionized water. Absorbance measurements were made at 340 nm. An initial absorbance measurement was made 4.5 sec after sample and deionized water addition and a second absorbance reading was taken ~8 min later after the reaction had gone to completion. The second absorbance reading was subtracted from the initial absorbance reading to determine the ΔA due to metabolism of the carbonate in the sample. A sample blank was ran to correct the Δ absorbance for dissolved carbon dioxide in the deionized water. Results are shown below.

| Sodium Carbonate (mmol/L) | ΔA at 340 nm |
|---|---|
| 10 | 0.389 |
| 20 | 0.842 |
| 30 | 1.188 |
| 40 | 1.513 |

As with the two component carbon dioxide reagent above, a linear relationship exists between the absorbance change, ΔA, and the sodium carbonate concentration.

One of the inherent stability problems with carbon dioxide reagents, especially for 1 component reagents, is the absorption of ambient carbon dioxide and subsequent metabolism according to the above series of enzyme coupled reactions. This results in the exhaustion of the reduced pyridine nucleotide cofactor and loss of functionality of the reagent to measure carbon dioxide. This is especially a problem when the reagents are setting uncapped for extended periods of time. To improve cofactor stability, a pyridine nucleotide regenerating system can be added which will reduce the oxidized cofactor back to its reduced form. There are many regenerating systems which will fulfill this function. In general, a dehydrogenase and reduced substrate that is capable of being oxidized by the oxidized cofactor are the major requirements. In the case of the NAD-analogs, the analogs however must be functional with the dehydrogenase.

Below are data generated with the above reagent, with and without the presence of a nucleotide regenerating system. The nucleotide regenerating system used was glucose4-phosphate dehydrogenase (microbial) and glucose6-phosphate. In the reagent above, with the nucleotide regenerating system, the glucose6-phosphate concentration was increased to 20 mmol/L. The carbon dioxide reagents were put in 4 ml polyethylene vials and set at room temperature (~22° C.) with the bottle caps removed. At various time intervals the reagents were tested for the amount of remaining reduced 3-pyridinealdehyde-NADH using the protocol above where the absorbance change at 340 nm was calculated after all the remaining reduced nucleotide cofactor had been metabolized after adding a 0.1 mol/L or 1 mol/L sodium carbonate sample.

ΔA at 340 nm

Hours or Days of Carbon Dioxide Reagent Stored at ~22° C. in uncapped 4 ml vial

| Carbon Dioxide Reagent | Time = | | | | |
|---|---|---|---|---|---|
| | 0 | 12 Hours | 24 Hours | 7 Days | 14 Days |
| a. No Nucleotide Regenerating System | 1.12 | 0.74 | 0.50 | | |
| b. Plus Nucleotide Regenerating System | 1.66 | | | 1.75 | 1.80 |

Without the nucleotide regenerating system, more than 50% of the 3-pyridinealdehyde-NADH has been metabolized after 24 hours. With the nucleotide regenerating system, however, virtually all the 3-pyridinealdehyde-NADH is recovered even after 14 days. The "apparent" increase in the nucleotide concentration with time in the uncapped vials with the nucleotide regenerating system is due evaporation and subsequent "concentration" of the reagent and the nucleotide.

The pyridine nucleotide regenerating system has also been found to extend the stability of reduced pyridine nucleotide cofactor analogs in other reagents. Reagents using NADH/NADPH analogs where improvements in analog stability was observed were with: ammonia, urea or BUN, ALT and AST. The nucleotide regenerating system was found especially useful with the ALT and AST reagents since it is nearly impossible to obtain lactate dehydrogenase and malate dehydrogenase that are totally devoid of contamination by ALT and AST.

EXAMPLE 8

One Component Liquid Ammonia Reagent

To ~100 ml deionized water is added 7.3 g bicine. After dissolving the pH is adjusted to ~8.0 with sodium hydroxide pellets. In order are added with dissolution: 5.6 mg $Na_2EDTA.2H_2O$, 376 mg adenosine 5'diphosphate (potassium salt dihydrate), 45 g xylitol, 150 mg bovine serum albumin and 135 mg sodium azide. The volume is brought to ~145 ml with deionized water and the pH is adjusted to 8.3 with 6 mol/L sodium hydroxide and diluted to 150 ml with deionized water. To three 10 ml aliquots of this solution were added the following:

Solution 1: 4.2 mg 3-pyridinealdehyde-NAD and 1.77 mg glucose-6-phosphate (sodium salt)

Solution 2: 5.1 mg 3-acetylpyridine-NAD and 1.94 mg glucose-6-phosphate (sodium salt)

Solution 3: 3.4 mg thionicotinamide-NAD and 1.26 mg glucose-6-phosphate (sodium salt)

Five Units glucose-6-phosphate dehydrogenase was added to each solution and the solutions were incubated at 37° C. After 6, 22, and 36 hours, Solutions 1, 2 and 3 respectively were removed from the incubation and to each solution was added 76 mg disodium α-ketoglutarate. To Solutions 1, 2 and 3 respectively was added 20 Units/ml, 75 Units/ml and 100 Units/ml glutamate dehydrogenase (bovine liver). The solutions were used in an ammonia assay using 100 ul reagent and 20 and 30 uls of sample for Solution 3, and 2 and 1 respectively. Deionized water was added with the samples to give a total volume of 150 ul for each assay. Assays were carried out at 37° C. The wavelengths used were 340 nm for 3-pyridinealdehyde-NADH and 3-acetylpyridine-NADH and 405 nm for thionicotinamide-NADH. To calculate the ΔA for each sample, an absorbance measurement 600 sec after sample and deionized water was added was subtracted from an absorbance measurement 4.5 seconds after sample and deionized water addition. Results are shown below.

| Ammonia (umol/L) | 3-Pyridinealdehyde-NADH ΔA 340 nm | 3-Acetylpyridine-NADH ΔA 340 nm | Thionicotinamide-NADH ΔA 405 nm |
| --- | --- | --- | --- |
| 50 | 0.029 | 0.033 | 0.050 |
| 100 | 0.063 | 0.055 | 0.093 |
| 200 | 0.124 | 0.093 | 0.166 |
| 300 | 0.199 | 0.182 | 0.280 |
| 400 | 0.259 | 0.229 | 0.363 |
| 500 | 0.339 | 0.315 | 0.426 |
| 600 | 0.392 | 0.368 | 0.537 |

The data shows a linear relationship between the absorbance change, ΔA, and the ammonia concentration. This demonstrates that ammonia can be quantitatively measured with the above NADH analogs.

EXAMPLE 9

One Component Liquid Urea Reagent

In 125 ml deionized water, dissolve 3.26 g bicine and adjust the pH to ~8.3 with sodium hydroxide pellets. Add in order with dissolution: 7.4 mg Na$_2$EDTA.2H$_2$O, 470 mg adenosine 5'-diphosphate (potassium salt dihydrate), 60 g xylitol and dilute to ~190 ml with deionized water. Add 200 mg bovine serum albumin, 100 mg sodium azide and after adjusting the pH to 8.5, dilute to 200 ml with deionized water. To three 10 ml aliquots add the following:

Solution 1: 5.5 mg 3-pyridinealdehyde-NAD and 2.30 mg glucose-6-phosphate (sodium salt)

Solution 2: 6.6 mg 3-acetylpyridine-NAD and 2.52 mg glucose-6-phosphate (sodium salt)

Solution 3: 4.4 mg thionicotinamide-NAD and 1.64 mg glucose-6-phosphate (sodium salt)

Five Units glucose-6-phosphate dehydrogenase was added to each solution and each solution was incubated at 37° C. as follows: Solution 1: 6 hours, Solution 2: 36 hours, Solution 3: 44 hours. Seventy-six mg disodium α-ketoglutarate and 500 Units urease were added to each solution followed by the addition of glutamate dehydrogenase as follows: Solution 1: 30 Units/ml, Solution 2: 15 Units/ml and Solution 3: 5 Units/ml. Aqueous urea samples were measured by adding 2 uls sample and 92 uls deionized water to 100 uls of Solution 1 or 2 and 200 uls Solution 3. Solutions 1 and 2 were ran as a rate assay over a 3.75 minute time interval just after sample was added while Solution 3 was ran as a 75 second assay. Results are as follows:

| Urea mmol/L | 3-Pyridinealdehyde-NADH ΔA/min at 340 nm | 3-Acetylpyridine-NADH ΔA/min at 340 nm | Thionicotinamide-NADH ΔA/75 seconds at 405 nm |
| --- | --- | --- | --- |
| 5 | 0.0039 | 0.0032 | 0.233 |
| 10 | 0.0092 | 0.0068 | 0.460 |
| 20 | 0.0191 | 0.0140 | 0.875 |
| 30 | 0.0275 | 0.0206 | 1.532 |
| 40 | 0;0382 | 0.0282 | 1.887 |
| 50 | 0.0481 | 0.0355 | — |

The data shows a linear relationship between the absorbance change, ΔA, and urea concentration. The data demonstrates that urea can be quantitatively measured with above NADH analogs.

EXAMPLE 10

One Component AST Liquid Reagent

To ~60 mls deionized water are added with dissolution: 1.45 g Tris, 5.58 g L-sodium aspartate, 30 g sorbitol, 90 mg sodium azide and 100 mg bovine gamma globulin. The pH was adjusted to 7.80 with 6 N HCl. To 10 mls of the reagent were added 5.6 mg 3-acetylpyridine-NAD, 14.1 mg glucose-6-phosphate (sodium salt) and ~1 Unit glucose-6-phosphate dehydrogenase. After a 12 hour incubation at 37° C., 34.2 mg disodium α-ketoglutarate, 4.1 mg Na$_2$EDTA.2H$_2$O and 500 Units malate dehydrogenase were added. A series of aqueous AST samples were ran and compared to a commercial IFCC AST reagent (without pyridoxal phosphate). Each reagent was ran using a 1:12 (sample:reagent volume) ratio and absorbance measurements were measured at 37° C. at 340 nm, starting measurements 50 seconds after sample addition and at 25 second intervals for 10 minutes. A linear search program used to determine the linear portion of the absorbance measurements for each sample. Results are shown below.

| Sample Dilution | U/L; 3-Acetylpyridine-NADH | U/L; Commercial IFCC AST Reagent |
| --- | --- | --- |
| 0.01 | 9.3 | 12 |
| 0.1 | 93 | 96 |
| 0.2 | 192 | 185 |
| 0.4 | 370 | 378 |
| 0.7 | 641 | 665 |

The data demonstrates that 3-acetylpyridine-NADH gives essentially the same results as the commercially available reagent using NADH. Thus, 3-acetylpyridine-NADH can be used to quantitate AST activity.

EXAMPLE 11

One Component ALT Liquid Reagent

To ~30 ml deionized water are added with dissolution: 1.82 g Tris, 6.42 g L-alanine, 428 mg α-ketoglutarate, 90 mg sodium azide and 100 mg bovine serum albumin. The solution is diluted to ~95 ml with deionized water, and after adjusting the pH to 7.5 with 6 N HCL diluted to 100 ml with deionized water. To 10 mls of the reagent are added 5.7 mg 3-acetylpyridine-NAD, 2.17 mg glucose-6-phosphate (sodium salt) and ~200 Units glucose-6-phosphate dehydrogenase. The solution was incubated at 37° C. for ~36 hours and after cooling to room temperature 50 Units lactate dehydrogenase (Staphylococcus sp.) was added. A series of aqueous ALT samples was ran as described for AST above and also ran in a commercial IFCC reagent (without pyridoxal phosphate). Results are shown below.

| Sample Dilution | U/L; 3-Acetylpyridine-NADH | U/L; Commercial IFCC ALT Reagent |
|---|---|---|
| 0.01 | 11 | 7 |
| 0.10 | 92 | 90 |
| 0.20 | 183 | 169 |
| 0.40 | 359 | 369 |
| 0.70 | 607 | 664 (× 2 dilution) |

The data demonstrates that 3-acetylpyridine NADH gives essentially the same results as the commercially available reagent using NADH. Thus, 3-acetylpyridine-NADH can be used to quantitate ALT activity.

EXAMPLE 12

One Component Liquid Triglyceride Reagent

The coupled enzyme reaction for measuring triglycerides is as follows:

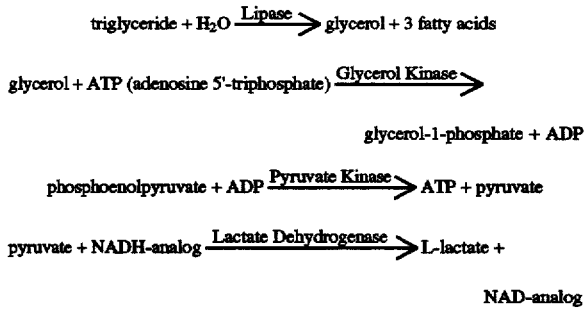

To ~80 ml deionized water are added in order with dissolution: 2.60 g (N-[2-hydroxyethyl]piperazine-N'-[2-ethanesulfonic acid]) sodium salt, 182 mg adenosine 5'-triphosphate disodium trihydrate salt, 203 mg magnesium chloride hexahydrate, 37 mg $Na_2EDTA.2H_2O$, 41 mg cholic acid, 50 mg bovine serum albumin and 90 mg sodium azide. The pH was adjusted to 7.5 with 6 N HCL and the volume brought to 100 ml with deionized water. After mixing, three 10 ml aliquots were removed and labeled A, B and C. To these solutions was added the following:

Solution A: 2.8 mg 3-pyridinealdehyde-NAD, 1.18 mg glucose-6-phosphate (sodium salt)

Solution B: 3.4 mg 3-acetylpyridine-NAD, 1.26 mg glucose-6-phosphate (sodium salt)

Solution C: 1.9 mg thionicotinamide-NAD, 0.70 mg glucose-6-phosphate (sodium salt).

After adding ~1 unit glucose-6-phosphate dehydrogenase, solutions A and B were incubated at 37° C. for 36 and 18 hours respectively and Solution C was incubated at room temperature (22° C.) for 24 hours. To each solution was added 46.6 mg phosphoenolpyruvate tri (monocyclohexylammonium) salt, 30 Units glycerokinase, 100 Units lipoprotein lipase and 30 Units pyruvate kinase. One thousand Units lactate dehydrogenase was added to solution A and 100 Units were added to Solutions B and C. Triglyceride assays were ran at 37° C. With Solutions A and B, 3 ul sample and 10 ul deionized water were added to 150 ul reagent. Absorbance readings at 340 nm were taken 4.5 seconds after sample addition and again after 12.1 minutes and 6.25 minutes for Solutions A and B. For Solution C, 2 ul sample and 10 ul deionized water were added to 200 ul reagent and absorbance readings at 405 nm were taken 4.5 seconds after sample addition and after 10 minutes. Below are the results using a series of aqueous dicaprin standards.

| Dicaprin mg/dl | 3-Pyridinealdehyde-NADH ΔA/12.1 min 340 nm | 3-Acetylpyridine-NADH ΔA/6.25 min 340 nm | Thionicotinamide-NADH ΔA/10 min 405 nm |
|---|---|---|---|
| 45 | 0.046 | 0.065 | 0.043 |
| 90 | 0.090 | 0.131 | 0.085 |
| 180 | 0.180 | 0.277 | 0.176 |
| 319 | 0.300 | 0.461 | 0.300 |
| 455 | 0.412 | 0.669 | 0.425 |

The data demonstrates a linear relationship between the absorbance change, ΔA, and the dicaprin concentration. Thus, triglycerides can be quantitatively determined using the above NADH analogs.

EXAMPLE 13

One Vial Liquid Pyruvic Acid Reagent

To ~40 mls deionized water are added with dissolution 1.3 g (N-[2-hydroxyethyl]-piper-azine-N'-[2-ethanesulfonic acid) sodium salt, 50 mg bovine serum albumin and 40 mg sodium azide. The pH was adjusted to 7.0 and the solution was diluted to 50 ml with deionized water. To 10 ml aliquots were added the following:

Solution A: 2.2 mg thionicotinamide-NAD and 0.81 mg glucose-6phosphate (sodium salt)

Solution B: 3.9 mg pyridinealdehyde-NAD and 1.57 mg glucose-6phosphate (sodium salt)

Solution C: 3.5 mg acetylpyridine-NAD and 1.34 mg glucose-6-phosphate (sodium salt)

After adding approximately 1 Unit of glucose-6-phosphate dehydrogenase to each solution, each solution was incubated as follows: Solution A—48 hours at room temperature (-22° C.), Solution B—48 hours at 37° C. and Solution C—24 hours at 37° C. Rabbit muscle lactate dehydrogenase was added to each solution to give the following activities: Solution A—7.5 U/mL, Solution B—100 U/mL, and Solution C—6 U/mL. A series of aqueous sodium pyruvate samples was assayed with the three solutions. For solution A, 5 ul sample, 15 ul deionized water and 150 ul reagent were used, for Solution B, 10 ul sample, 40 ul deionized water and 100 ul reagent were used, and for Solution C, 10 ul sample, 15 ul deionized water and 150 ul reagent were used. Solution A and C were ran as end point assays where the final absorbance reading was subtracted from the initial absorbance reading 4.5 seconds after sample and deionized water addition. Solution B was ran as a rate assay. All assays were performed at 37° C. Results were as follows:

| Pyruvate mmol/L | 3-Pyridinealdehyde-NADH ΔA/10 min at 340 nm | 3-Acetylpyridine-NADH ΔA/5.8 min at 340 nm | Thionicotinamide-NADH ΔA/13.6 min at 405 nm |
|---|---|---|---|
| 0.5 | 0.074 | 0.100 | 0.086 |
| 1.0 | 0.145 | 0.206 | 0.187 |
| 2.0 | 0.311 | 0.416 | 0.384 |
| 3.0 | 0.457 | 0.619 | 0.580 |
| 4.0 | 0.594 | 0.805 | 0.751 |
| 5.0 | 0.743 | 1.004 | 0.915 |

The data demonstrates a linear relationship between the absorbance change, ΔA, and the pyruvate concentration. Thus, pyruvic acid can be quantitatively measured using the above NADH analogs.

EXAMPLE 14

Creatine Kinase Procedure

Creatine Kinase can be determined with the following procedure using NADH-analogs.

creatine + ATP $\xrightarrow{\text{Creatine Kinase}}$ ADP + creatine phosphate

ADP + phosphoenolpyruvate $\xrightarrow{\text{Pyruvate Kinase}}$ pyruvate + ATP pyruvate + NADH-analog $\xrightarrow{\text{Lactate Dehydrogenase}}$ L-lactate + NAD-analog In this coupled enzyme procedure the activity of creatine kinase can be determined by the rate of oxidation of the NADH-analog in the presence of a divalent metal such as magnesium. A kit for carrying out this measurement would include, for example, thionicotinamide-NADH, 3-acetylpyridine-NADH, or 3-pyridinealdehyde-NADH; a buffer; creatine; pyruvate kinase; lactate dehydrogenase; adenosine 5'-triphosphate; and phosphoenolpyruvate.

EXAMPLE 15

ATP (Adenosine 5'-triphosphate) Procedure

ATP can be determined using the following coupled enzymatic procedure using NADH-analogs.

ATP + 3-phosphoglycerate $\xrightarrow{\text{Phosphoglyceric Phosphokinase}}$ ADP + 1,3-diphosphoglycerate 1,3-diphosphoglycerate + NADH-analog $\xrightarrow{\text{Glyceraldehyde Phosphate Dehydrogenase}}$ glyceraldehyde-3-phosphate + NAD-analog In this coupled enzyme assay, conducted in the presence of a divalent metal such as magnesium, the quantity of NADH-analog oxidized by 1,3-diphosphoglycerate will be equal to the quantity of ATP in the sample. A kit for carrying out this measurement would include, for example, thionicotinamide-NADH thionicotinamide-NADPH, 3-acetylpyridine-NADH, 3-acetylpyridine-NADPH, 3-pyridinealdehyde-NADH, or 3-pyridinealdehyde-NADPH; a buffer; 3-phosphoglycerate; phosphoglyceric phosphokinase; and glyceraldehyde phosphate dehydrogenase.

EXAMPLE 16

Determination of 2,3-Diphosphoglyceric Acid

The following enzyme coupled procedure can be used to measure 2,3-diphosphoglyceric acid.

2,3-diphosphoglyceric acid $\xrightarrow[\text{(2-Phosphoglycolic Acid)}]{\text{Phosphoglycerate Mutase}}$ 3-phosphoglycerate + phosphate 3-phosphoglycerate + ATP $\xrightarrow{\text{Phosphoglyceric Phosphokinase}}$ 1,3-diphosphoglycerate + ADP 1,3 diphosphoglycerate + NADH-analog $\xrightarrow{\text{Glyceraldehyde Phosphate Dehydrogenase}}$ glyceraldehyde-3-phosphate + NAD-analog In this procedure, conducted in the presence of a divalent metal such as magnesium, the quantity of NADH-analog oxidized will be equal to the quantity of 2,3-diphosphoglycerate in the sample. A kit useful for carrying out this determination would include, for example, thionicotinamide-NADH, thionicotinamide-NADPH, 3-acetylpyridine-NADH, 3-acetylpyridine-NADPH, 3-pyridinealdehyde-NADH or 3-pyridinealdehyde-NADPH; a buffer; adenosine 5'-triphosphate; phosphoglycerate mutase; 2-phosphoglycolic acid; phosphoglyceric phosphokinase; and glyceraldehyde phosphate dehydrogenase.

EXAMPLE 17

Sorbitol Dehydrogenase Determination

Sorbitol dehydrogenase activity can be determined using the following procedure.

fructose + NADH-analog $\xrightarrow{\text{Sorbitol Dehydrogenase}}$ sorbitol + NAD-analog In this procedure the activity of sorbitol dehydrogenase will be equal to the rate of oxidation of the NADH-analog. A kit useful for carrying out this determination would include, for example, thionicotinamide-NADH 3-acetylpyridine-NADH or 3-pyridinealdehyde-NADH; a buffer, and fructose.

EXAMPLE 18

Lactate Dehydrogenase Determination

Lactate dehydrogenase activity can be determined using the following procedure.

pyruvic acid+NADH-analog Lactate Dehydrogenase→L-lactic acid+NAD-analog

In this procedure the activity of lactate dehydrogenase will be equal to the rate of oxidation of the NADH-analog. A kit useful for carrying out this determination would include, for example, 3-acetylpyridine-NADH 3-pyridinealdehyde-NADH or thionicotinamide-NADH; a buffer; and pyruvic acid.

EXAMPLE 19

αHydroxybutyrate Dehydrogenase Determination

α-Hydroxybutyrate dehydrogenase activity can be determined using the following procedure.

α-ketobutyrate+NADH-analog α-Hydroxybutyrate Dehydrogenase→α-hydroxybutyrate+NAD-analog In this procedure the activity of a-hydroxybutyrate dehydrogenase activity will be equal to the rate of oxidation of the NADH-analog. A kit useful for carrying out this determination would include 3-acetylpyridine-NADH, 3-pyridinealdehyde-NADH or thionicotinamide-NADH; a buffer; and α-hydroxybutyrate.

EXAMPLE 20

Procedure for Measuring Salicylates

The following procedure can be used to measure salicylates in samples.

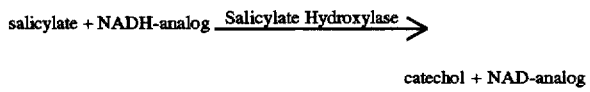

In this procedure the quantity of salicylate will be equal to the quantity of NADH-analog oxidized. A kit useful for carrying out this determination on would include, for example, 3-acetylpyridine-NADH, 3-pyridinealdehyde-NADH or thionicotinamide-NADH; a buffer; and salicylate dehydrogenase.

EXAMPLE 21

Procedure for Measuring 5'-Nucleotidase Activity

The following procedure can be used to determine 5'-nucleotidase activity.

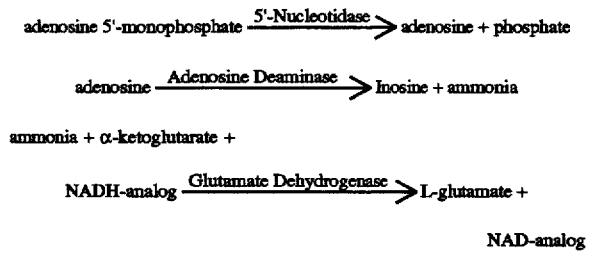

In this procedure the activity of 5'-nucleotidase will be equal to the rate of oxidation of the NADH-analog. A kit useful for carrying out this determination would include, for example, thionicotinamide-NADH, thionicotinamide-NADPH, 3-acetylpyridine-NADH, 3-acetylpyridine-NADPH, 3-pyridinealdehyde-NADH, or 3-pyridinealdehyde-NADPH; a buffer; adenosine 5'-monophosphate; adenosine deaminase; alpha-ketoglutarate, glutamate dehydrogenase.

What is claimed is:

1. A diagnostic reagent kit comprising a compound of the formula: (I)

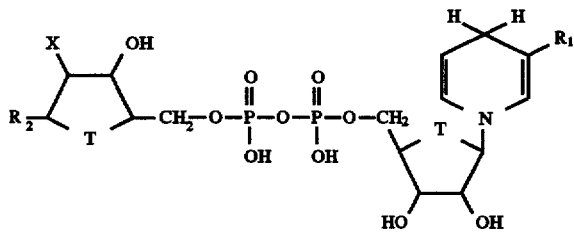

wherein:

$R_1$ is
$R_2$ is an aryl or heteroaryl;
Q is C or S;
T is O or S;
X is H, $OR_3$ or $H_2PO_4$, where $R_3$ is H, $C_{1-4}$ alkyl, $C_{1-4}$ haloalkyl, $C_{1-4}$ subtituted alkyl or halogen;
Y is O, S or NOH; and
Z is H, $C_{1-6}$ alkyl, $C_{1-6}$ haloalkyl, $C_{1-6}$ substituted alkyl, NHL where L is H, OH or $NH_2$, aryl or aralkyl except that L is not H when $R_2$ is adenine.

2. The diagnostic kit of claim 1, further comprising an enzyme.

3. The diagnostic kit of claim 2, wherein said enzyme is selected from the group consisting of lactate dehydrogenase, malate dehydrogenase, glutamate dehydrogenase, phosphoenolpyruvate carboxylase, urease, pyruvate kinase, phosphoglyceric phosphokinase, phosphoglycerate mutase, glycerol kinase, glyceraldehyde phosphate dehydrogenase, adenosine deaminase and salicylate hydroxylase.

4. The diagnostic kit of claim 1, further comprising a buffer.

5. The diagnostic kit of claim 1, further comprising a substrate.

6. The diagnostic kit of claim 1, wherein $R_2$ is an adenine.

7. The diagnostic kit of claim 1, wherein X is OH.

8. The diagnostic kit of claim 1, wherein X is $H_2PO_4$.

9. The diagnostic kit of claim 1, wherein each T is O.

10. The diagnostic kit of claim 1, wherein $R_1$ is

11. The diagnostic kit of claim 1, wherein $R_1$ is

12. The diagnostic kit of claim 1, wherein $R_1$ is

13. The diagnostic kit of claim 1, wherein said compound of Formula (I) is selected from the group consisting of 3-pyridinealdehyde-NADH, 3-pyridinealdehyde-NADPH 3-acetylpyridine-NADH, 3-acetylpyridine-NADPH, thionicotinamide-NADH and thionicotinamide-NADPH.

14. The diagnostic kit of claim 1, wherein wherein $R_1$ is selected from the group consisting of

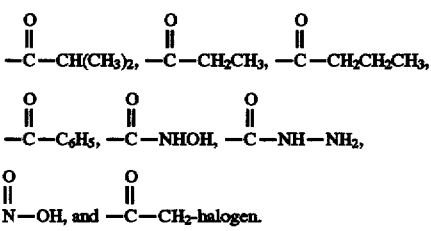

15. A kit in accordance with claim 1 for measuring carbon dioxide, comprising:
a) a compound of Formula (I) selected from the group consisting of 3-pyridinealdehyde-NADH, 3-acetylpyridine-NADH and 3-thionicotinamide-NADH;
b) a buffer;
c) phosphoenolpyruvate;
d) malate dehydrogenase;
e) a divalent metal ion; and
f) phosphoenolpyruvate carboxylase.

16. The diagnostic kit of claim 1, wherein said compound of Formula (I) is maintained in a buffer solution having a pH of from about 5.5 to about 9.5.

17. The diagnostic kit of claim 1, wherein said compound of Formula (I) is maintained in dry form.

18. A kit in accordance with claim 1 for measuring ammonia, comprising:
   a) a compound of Formula (I) selected from the group consisting of 3-acetylpyridine-NADH, 3-acetylpyridine-NADPH, thionicotinamide-NADH, thionicotinamide-NADPH, 3-pyridinealdehyde-NADH and 3-pyridinealdehyde-NADPH;
   b) a buffer;
   c) α-ketoglutarate; and
   d) glutamate dehydrogenase.

19. A kit in accordance with claim 1 for measuring urea, comprising:
   a) a compound of Formula (I) selected from the group consisting of 3-acetylpyridine-NADH, 3-acetylpyridine-NADPH, 3-pyridinealdehyde-NADH, 3-pyridinealdehyde-NADPH, thionicotinamide-NADH and thionicotinamide-NADPH;
   b) a buffer;
   c) α-ketoglutarate;
   d) glutamate dehydrogenase; and
   e) urease.

20. A kit in accordance with claim 1 for measuring pyruvic acid, comprising:
   a) a compound of Formula (I) selected from the group consisting of thionicotinamide-NADH, 3-acetylpyridine-NADH and 3-pyridinealdehyde-NADH;
   b) a buffer; and
   c) lactate dehydrogenase.

21. A kit in accordance with claim 1 for measuring alanine aminotransferase, comprising:
   a) a compound of Formula (I) selected from the group consisting 3-acetylpyridine-NADH, 3-pyridinealdehyde-NADH and thionicotinamide-NADH;
   b) a buffer;
   c) L-alanine;
   d) α-ketoglutarate; and
   e) lactate dehydrogenase.

22. A kit in accordance with claim 1 for measuring aspartate aminotransferase, comprising:
   a) a compound of Formula (I) selected from the group consisting of 3-acetylpyridine-NADH, 3-pyridinealdehyde-NADH and thionicotinamide-NADH;
   b) a buffer;
   c) α-ketoglutarate;
   d) L-aspartate; and
   e) malate dehydrogenase.

23. The kit of claim 22, further comprising an oxamate.

24. The kit of claim 22, further comprising lactate dehydrogenase.

25. A kit in accordance with claim 1 for measuring lactate dehydrogenase, comprising:
   a) a compound of Formula (I) selected from the group consisting of 3-acetylpyridine-NADH, 3-pyridinealdehyde-NADH and thionicotinamide-NADH;
   b) a buffer; and
   c) pyruvic acid.

26. A kit in accordance with claim 1 for measuring salicylates, comprising:
   a) a compound of Formula (I) selected from the group consisting of 3-acetylpyridine-NADH, 3-pyridinealdehyde-NADH and thionicotinamide-NADH;
   b) a buffer; and
   c) salicylate dehydrogenase.

27. A kit in accordance with claim 1, further comprising a nucleotide regenerating system.

28. A kit in accordance with claim 1 for measuring α-hydroxybutyrate activity, comprising:
   a) a compound of Formula (I) selected from the group consisting of 3-acetylpyridine-NADH, 3-pyridinealdehyde-NADH and thionicotinamide-NADH;
   b) a buffer; and
   c) α-hydroxybutyrate.

29. A kit in accordance with claim 1 for measuring adenosine 5'-triphosphate, comprising:
   a) a compound of Formula (I) selected from the group consisting of thionicotinamide-NADH thionicotinamide-NADPH, 3-acetylpyridine-NADP, 3-acetylpyridine-NADPH, 3-pyridinealdehyde-NADH and 3-pyridinealdehyde-NADPH;
   b) a buffer;
   c) 3-phosphoglycerate;
   d) phosphoglyceric phosphokinase;
   e) a divalent metal ion; and
   f) glyceraldehyde phosphate dehydrogenase.

30. A kit in accordance with claim 1 for measuring 2,3-diphosphoglyceric acid, comprising:
   a) a compound of Formula (I) selected from the group consisting of thionicotinamide-NADIR thionicotinamide-NADPH 3-acetylpyridine-NADH, 3-acetylpyridine-NADPH, 3-pyridinealdehyde-NADH and 3-pyridinealdehyde-NADPH;
   b) a buffer
   c) adenosine 5'-triphosphate;
   d) phosphoglycerate mutase;
   e) 2-phosphoglycolic acid;
   f) phosphoglyceric phosphokinase;
   g) a divalent metal ion; and
   h) glyceraldehyde phosphate dehydrogenase.

31. A kit in accordance with claim 1 for measuring sorbitol dehydrogenase, comprising:
   a) a compound of Formula (I) selected from the group consisting of thionicotnamide-NADH, 3-acetylpyridine-NADH and 3-pyridinealdehyde-NADH,
   b) a buffer;and
   c) fructose.

32. A kit in accordance with claim 1 for measuring triglycerides, comprising:
   a) a compound of Formula (I) selected from the group consisting of thionicotinamide-NADH 3-acetylpyridine-NADH and 3-pyridinealdehyde-NADH;
   b) an enzyme selected from the group consisting of lipase and lipoprotein lipase and mixtures thereof;
   c) phosphoenolpyruvate;
   d) pyruvate kinase;
   e) lactate dehydrogenase;
   f) a divalent metal ion;

g) a bile acid;

h) adenosine 5'-triphosphate; and i) glycerol kinase.

33. A kit in accordance with claim 1 for measuring creatine kinase, comprising:

a) a compound of Formula (I) selected from the group consisting of thionicotinamide-NADH, 3-acetylpyridine-NADH and 3-pyridinealdehyde-NADH;

b) a buffer;

c) creatine;

d) pyruvate kinase;

e) lactate dehydrogenase;

f) adenosine 5'-triphosphate;

g) a divalent metal ion; and h) phosphoenolpyruvate.

34. A kit in accordance with claim 1 for the measurement of 5'-nucleotidase, comprising:

a) a compound of Formula (I) selected from the group consisting of thionicotinamide-NADH, thionicotinamide-NADPH, 3-acetylpyridine-NADH 3-acetylpyridine-NADPH, 3-pyridinealdehyde-NADH and 3-pyridinealdehyde-NADPH;

b) a buffer;

c) adenosine 5'-monophosphate;

d) adenosine deaminase; and e) glutamate dehydrogenase; and f) alpha ketoglutarate.

35. A method of quantifying the presence of an enzyme or analyte in a sample, comprising:

a) contacting said sample with a compound of the formula:

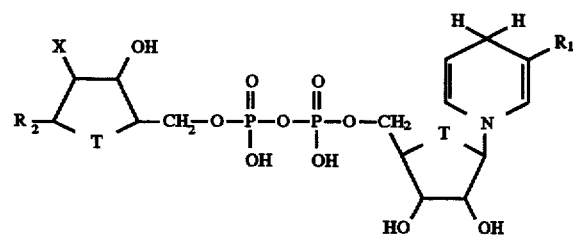

wherein:

$R_1$ is

$R_2$ is an aryl or heteroaryl;

Q is C or S;

T is O or S;

X is H, $OR_3$ or $H_2PO_4$, where $R_3$ is H, $C_{1-4}$ alkyl, $C_{1-4}$ haloalkyl, $C_{1-4}$ subtituted alkyl or halogen;

Y is O, S or NOH; and

Z is H, $C_{1-6}$ alkyl, $C_{1-6}$ haloalkyl, $C_{1-6}$ substituted alkyl, NHL where L is H, OH or $NH_2$, aryl or aralkyl except that L is not H when $R_2$ is adenine; and b) measuring the change of absorbance or fluorescence resulting from said contacting step a).

36. The method of claim 35, further comprising conducting said contacting step a) in the presence of a buffer.

37. The method of claim 35, further comprising conducting said contacting step a) in the presence of a substrate.

38. The method of claim 35, wherein $R_1$ is selected from the group consisting of

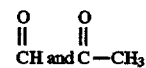

and said absorbance is measured over from about 320 to about 410 nanometers.

39. The method of claim 35, wherein $R_1$ is

and said absorbance is measured over from about 360 to about 440 nanometers.

40. The method of claim 35, wherein $R_2$ is an adenine.

41. The method of claim 35, wherein X is OH.

42. The method of claim 35, wherein X is $H_2PO_4$.

43. The method of claim 35, wherein each T is O.

44. The method of claim 35, wherein said enzyme or analyte in said sample is selected from the group consisting of carbon dioxide, ammonia, urea, blood urea nitrogen, pyruvate, alanine amninotransferase, aspartate aminotransferase, salicylates, triglycerides, 2,3-diphosphoglyceric acid, adenosine 5'-triphosphate, lactate dehydrogenase, α-hydroxybutyrate dehydrogenase, sorbitol dehydrogenase, 5'-nucleotidase and creatine kinase.

* * * * *